(12) United States Patent
Burnett

(10) Patent No.: US 9,427,556 B2
(45) Date of Patent: Aug. 30, 2016

(54) METHODS FOR TREATMENT OF A BODY CAVITY OR LUMEN

(75) Inventor: Daniel Rogers Burnett, San Francisco, CA (US)

(73) Assignee: Channel Medsystems, Inc., Emeryville, CA (US)

(*) Notice: Subject to any disclaimer, the term of this patent is extended or adjusted under 35 U.S.C. 154(b) by 685 days.

(21) Appl. No.: 13/306,076

(22) Filed: Nov. 29, 2011

(65) Prior Publication Data
US 2012/0136343 A1    May 31, 2012

Related U.S. Application Data

(63) Continuation of application No. PCT/US2010/036947, filed on Jun. 1, 2010.

(60) Provisional application No. 61/337,648, filed on Feb. 11, 2010, provisional application No. 61/277,770, filed on Sep. 30, 2009, provisional application No. 61/217,537, filed on Jun. 1, 2009.

(51) Int. Cl.
| | |
|---|---|
| *A61M 25/10* | (2013.01) |
| *A61B 18/04* | (2006.01) |
| *A61B 18/00* | (2006.01) |
| *A61M 25/00* | (2006.01) |
| *A61M 25/01* | (2006.01) |

(52) U.S. Cl.
CPC .............. *A61M 25/10* (2013.01); *A61B 18/04* (2013.01); *A61B 2018/00023* (2013.01); *A61B 2018/046* (2013.01); *A61M 2025/0002* (2013.01); *A61M 2025/0003* (2013.01); *A61M 2025/0175* (2013.01); *A61M 2025/1015* (2013.01); *A61M 2025/1052* (2013.01); *A61M 2210/105* (2013.01); *A61M 2210/1433* (2013.01)

(58) Field of Classification Search
CPC .......... A61B 2018/00005; A61B 2018/00011; A61B 2018/00017; A61B 2018/0225; A61B 18/02; A61B 18/0218; A61B 18/04
USPC ................................ 606/21, 27; 607/96, 105
See application file for complete search history.

(56) References Cited

U.S. PATENT DOCUMENTS

| | | | | |
|---|---|---|---|---|
| 2,849,002 | A * | 8/1958 | Oddo | ............................ 606/192 |
| 4,044,401 | A * | 8/1977 | Guiset | ..................... A61F 2/042 |
| | | | | 128/DIG. 25 |
| 5,484,384 | A * | 1/1996 | Fearnot | ............................. 600/3 |
| 6,066,132 | A * | 5/2000 | Chen et al. | ...................... 606/28 |
| 6,283,959 | B1 * | 9/2001 | Lalonde | ................. A61B 18/02 |
| | | | | 606/21 |

(Continued)

FOREIGN PATENT DOCUMENTS

WO     WO 92/13271     8/1992

*Primary Examiner* — Christopher A Flory
(74) *Attorney, Agent, or Firm* — Levine Bagade Han LLP

(57) ABSTRACT

Methods and apparatus for the treatment of a body cavity or lumen are described where a heated fluid and/or gas may be introduced through a catheter and into treatment area within the body contained between one or more inflatable/expandable members. The catheter may also have optional pressure sensing elements which may allow for control of the pressure within the treatment zone and also prevent the pressure from exceeding a pressure of the inflatable/expandable members to thereby contain the treatment area between these inflatable/expandable members. Optionally, a chilled or room temperature fluid such as water may then be used to rapidly terminate the treatment session.

41 Claims, 12 Drawing Sheets

(56) References Cited

U.S. PATENT DOCUMENTS

| | | | |
|---|---|---|---|
| 6,575,932 B1* | 6/2003 | O'Brien et al. | 604/101.01 |
| 6,648,879 B2* | 11/2003 | Joye et al. | 606/21 |
| 7,727,147 B1 | 6/2010 | Osorio et al. | |
| 8,149,418 B2* | 4/2012 | Tearney | A61B 5/0062 356/479 |
| 8,384,907 B2* | 2/2013 | Tearney | A61B 5/0062 356/456 |
| 2002/0068860 A1 | 6/2002 | Clark | |
| 2003/0125613 A1 | 7/2003 | Enegren et al. | |
| 2003/0187428 A1* | 10/2003 | Lane | A61B 18/02 606/21 |
| 2004/0044375 A1* | 3/2004 | Diederich et al. | 607/27 |
| 2004/0082859 A1* | 4/2004 | Schaer | 600/459 |
| 2005/0065556 A1 | 3/2005 | Reghabi et al. | |
| 2005/0107855 A1 | 5/2005 | Lennox et al. | |
| 2005/0209587 A1* | 9/2005 | Joye | A61B 18/02 606/21 |
| 2006/0030843 A1* | 2/2006 | Lane | A61B 18/02 606/21 |
| 2007/0083126 A1* | 4/2007 | Marko et al. | 600/505 |
| 2007/0203396 A1 | 8/2007 | McCutcheon et al. | |
| 2007/0237739 A1 | 10/2007 | Doty | |
| 2008/0086042 A1 | 4/2008 | Brister et al. | |
| 2008/0097468 A1* | 4/2008 | Adams et al. | 606/119 |
| 2008/0097469 A1* | 4/2008 | Gruber et al. | 606/119 |
| 2008/0097470 A1* | 4/2008 | Gruber | A61B 17/12099 606/119 |
| 2008/0097471 A1* | 4/2008 | Adams et al. | 606/119 |
| 2008/0172041 A1* | 7/2008 | Shehata | A61M 25/04 604/544 |
| 2008/0245371 A1* | 10/2008 | Gruber | 128/831 |
| 2008/0300571 A1* | 12/2008 | LePivert | 604/503 |
| 2009/0018424 A1 | 1/2009 | Kamath et al. | |
| 2009/0076573 A1 | 3/2009 | Burnett et al. | |
| 2010/0016839 A1* | 1/2010 | Shehata | A61M 25/04 604/544 |
| 2010/0087798 A1* | 4/2010 | Adams et al. | 604/515 |
| 2010/0094270 A1* | 4/2010 | Sharma | 606/27 |
| 2010/0130970 A1* | 5/2010 | Williams et al. | 606/21 |
| 2010/0204688 A1* | 8/2010 | Hoey et al. | 606/27 |
| 2011/0054488 A1* | 3/2011 | Gruber et al. | 606/119 |
| 2012/0016273 A1* | 1/2012 | Diederich | 601/3 |
| 2012/0165641 A1 | 6/2012 | Burnett et al. | |
| 2012/0197245 A1* | 8/2012 | Burnett et al. | 606/21 |
| 2012/0310269 A1* | 12/2012 | Fearnot et al. | 606/191 |
| 2013/0023731 A1* | 1/2013 | Saadat et al. | 600/129 |
| 2013/0072786 A1* | 3/2013 | Keogh et al. | 600/424 |
| 2013/0296837 A1* | 11/2013 | Burnett et al. | 606/21 |
| 2014/0005648 A1* | 1/2014 | Burnett et al. | 606/21 |
| 2014/0005649 A1* | 1/2014 | Burnett et al. | 606/21 |
| 2014/0005650 A1* | 1/2014 | Burnett et al. | 606/21 |
| 2014/0012156 A1* | 1/2014 | Burnett et al. | 600/549 |
| 2014/0012235 A1* | 1/2014 | Pinchuk et al. | 604/544 |
| 2014/0012243 A1* | 1/2014 | Burnett et al. | 606/21 |
| 2014/0012244 A1* | 1/2014 | Burnett et al. | 606/21 |
| 2014/0025055 A1* | 1/2014 | Burnett et al. | 606/21 |
| 2014/0074081 A1* | 3/2014 | Burnett et al. | 606/21 |
| 2014/0088579 A1* | 3/2014 | Burnett et al. | 606/21 |
| 2014/0107404 A1* | 4/2014 | Gruber | 600/37 |
| 2015/0126990 A1* | 5/2015 | Sharma et al. | 606/30 |
| 2015/0141984 A1* | 5/2015 | Loomas | A61B 18/08 606/41 |
| 2015/0173943 A1* | 6/2015 | Loomas et al. | A61F 7/123 |

* cited by examiner

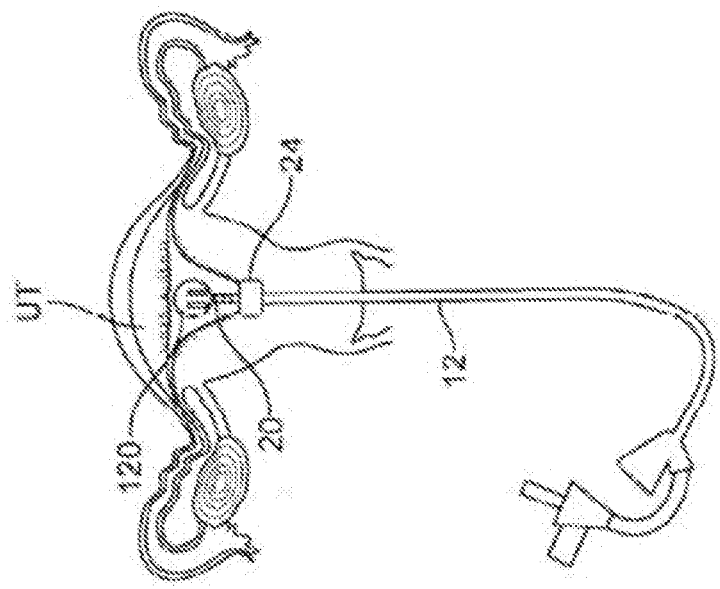
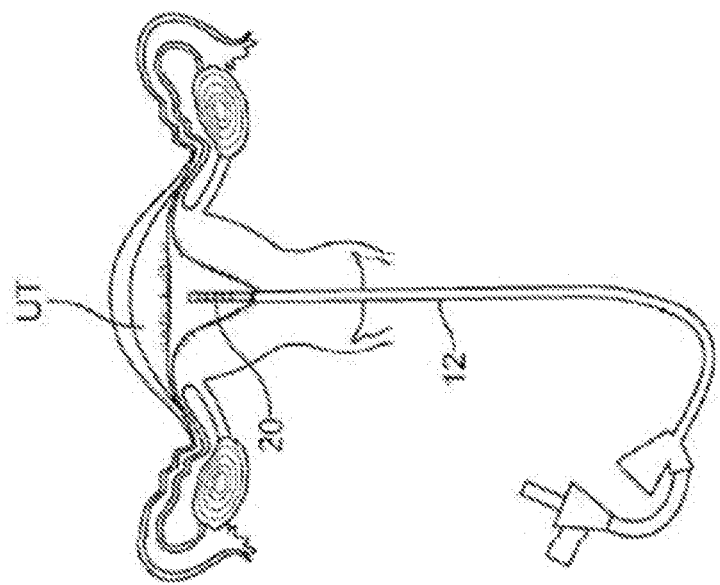
FIG. 12A
FIG. 12B

METHODS FOR TREATMENT OF A BODY CAVITY OR LUMEN

CROSS-REFERENCE TO RELATED APPLICATIONS

This application is a continuation of PCT International Patent Application No. PCT/US2010/036947 filed Jun. 1, 2010 which claims priority to U.S. Prov. 61/217,537 filed Jun. 1, 2009; 61/277,770 filed Sep. 30, 2009; and 61/337,648 filed Feb. 11, 2010, each of which is incorporated herein by reference in its entirety.

FIELD OF THE INVENTION

The present invention relates to medical devices. In particular, the present invention relates to methods and apparatus for therapeutic devices capable of exposing areas of the body to elevated or decreased temperatures, in a highly controlled manner.

BACKGROUND OF THE INVENTION

In the last few decades, therapeutic intervention within a body cavity or lumen has developed rapidly with respect to delivery of energy via radiofrequency ablation. While successful in several arenas, radiofrequency ablation has several major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

The current state of the art would benefit from minimally invasive devices and methods which deliver thermal energy to a desired area or extract energy from a desired area, in a consistent, controlled manner that does not char or freeze tissues or create excessive risk of unwanted organ or lumen damage.

SUMMARY OF THE INVENTION

When bodily tissues are exposed to even slightly elevated temperatures (e.g., 42 degrees C. or greater), focal damage may occur. If the tissues are exposed to temperatures greater than, e.g., 50 degrees C., for an extended period of time, tissue death will occur. The energy delivered by RF can then be excessive while a more controlled treatment can be achieved with heated fluids and/or vapors.

Generally, devices for delivering controlled treatment may comprise a source for a heated fluid and/or gas, e.g., hot water/steam, one or more pumps to deliver said hot water/steam, a catheter having one or more lumens defined therethrough and also having one or more ports to deliver or circulate the heated fluid and/or gas, e.g., hot water and/or vapor, to a controlled site in a controlled manner. The catheter may also have optional pressure sensing elements. The optional pressure sensing elements may allow the operator to monitor and/or control the pressure within the treatment zone and also prevent the pressure from becoming too high. The treatment site may be delineated by inflatable or expandable members which are pressurized or expanded to a target pressure to form a seal with the body cavity/lumen. The heated fluid and/or gas may then be delivered to the area contained by the inflatable/expandable members at a pressure that is less than that of the inflatable/expandable members thereby effectively containing the treatment area between these inflatable/expandable members. Optionally, a chilled or room temperature fluid such as water may then be used to rapidly terminate the treatment session.

The catheter having the inflatable/expandable members and optional pressure-sensing elements may be fitted within the lumen of an endoscope or other visualization device allowing the therapy to be delivered under direct visualization. In addition to direct visualization, this advance allows the scope to function as an insulator for the treatment catheter, thereby preventing unwanted exposure of body cavities/lumens to the elevated temperatures found in the heated fluid and/or gas coursing within the treatment catheter.

Generally, the heated fluid and/or gas may be heated to a temperature of between, e.g., 50 and 100 degrees Celsius. Exposure to these less elevated temperatures may allow for more controlled tissue damage and may obviate issues typically associated with the higher energy forms of treatment. It is understood and known in the art that the lower the temperature, the longer the dwell/treatment time needed. One treatment modality may be to deliver the heated fluid and/or gas at a temperature of, e.g., about 70 degrees C. for 5 minutes. Another modality may be to treat the tissue with the heated fluid and/or gas at a temperature of, e.g., 90 degree C. for 30 secs.

Among other features, the system may also include 1) the ability to thoroughly treat the treatment area due to the use of confining balloon(s) and/or use of an umbrella-like seal and use of a pressurized heated fluid and/or gas as the energy delivery medium, 2) the ability to treat relatively large areas in a very controlled manner due to the adjustable relationship between the two treatment-area defining inflatable/expandable components (e.g. balloon(s) and/or an umbrella-like seal), 3) the ability to form a fluid and/or gas-tight seal between the balloon(s) (and/or an umbrella-like seal) due to the catheter for the distal balloon traveling within the lumen of the proximal balloon catheter (avoidance of leakage around the catheters that the balloons can seal about), 4) the optional ability to monitor and control the pressure within the treatment area to ensure that the treatment area is not exposed to excessive pressures and that the pressure in the treatment area is prohibited from exceeding a pressure of the treatment area defining balloons, 5) the ability to ablate to a controlled depth in a reliable manner due to the lower energy and longer exposure times which allow the submucosa to cool itself with incoming blood flow, 6) the optional ability to fit within a working channel of an endoscope so that the device need not be inserted in a blind manner, 7) the ability to combine thermal or cooling therapy with delivery of active agents (e.g., anesthetic for pre-treatment of the target area or a chemotherapeutic for the treatment cancer or precancerous lesions, etc.), 8) the ability to fill the treatment defining area with fluid (e.g. cool, warm or room temperature fluid) capable of neutralizing the thermal or cooling energy in the treatment area in order to prevent potential damage caused by balloon rupture or seepage around the balloon and/or expandable member, 9) the ability to pre-chill (or pre-warm) the treatment area so that the submucosal tissues can be protected against the elevated (or cooling) temperature to which the lumen or bodily organ is being exposed, 10) the ability to adjust the treatment temperature time and/or temperature, 11) the ability to have modular, automated or semi-automated components and controls for handling the cooling, heating, inflations, deflations, infusions and/or extractions, 12) the ability to treat through the working channel of an endoscope or alongside an endoscope, 13) the ability to treat through a variety of endoscopes, e.g. nasal, gastrointestinal, esophageal, etc., 14) the ability to use off-the-shelf and/or disposable components to handle the fluid and pressure controls, or to use an automated or semi-automated system.

Additionally, the system may also incorporate features that may allow for efficacious therapy. For example, the system may utilize a sub-zero degrees Celsius temperature fluid lavage. This cold lavage may allow for much better control than charring and heating of the tissue and instead may provide a consistent depth of ablation in a manner that allows for rapid recovery and minimal post-operative pain (as opposed to heating methods). In addition, by using lavage of a fluid rather than cryogenic sprays (e.g., sprays which rely on the judgment of the user for determining time of spray application or spray location, etc.), the potential for over-ablation may be avoided. Also, the relatively colder cryogenic sprays have been found, in many cases, to result in damage to the endoscope while the higher temperatures possible with the system described herein (e.g., anywhere from −5 degrees Celsius to −80 degrees Celsius) is much less likely to damage the delivery equipment.

Secondly, the apparatus may utilize an umbrella-like element in the gastric space to allow for ablation of tissue regions, such as the lower esophageal sphincter at the gastroesophageal junction. This ablation is generally difficult to perform using balloon-based ablation technologies due to the expansion of the sphincter into the stomach. By utilizing an expandable, umbrella-like structure to form a firm seal at this site while allowing the ablation fluid and/or gas (heated or chilled) to contact the entire gastroesophageal junction. In addition, a spring-loaded element or other external force mechanism may be incorporated to provide for steady pressure and a firm seal against the stomach lining.

The apparatus may also be utilized with or without a balloon in body lumens or cavities that can be otherwise sealed. For example, a hypothermic fluid lavage of the uterus may be accomplished by introducing a subzero (Celsius) fluid into the uterus via cannulation of the uterus with a tube or cannula. If the tube is of sufficient diameter, backflow of the hypothermic lavage into the cervix and vagina may be prevented without the need for a balloon to contain the fluid. Use of balloons may be avoided for this particular type of application. In utilizing a hypothermic lavage, a fluid may be used that remains fluid even at subzero temperatures. This fluid may then circulated in the lumen (with or without a balloon) in order achieve ablation.

In using a hypothermic fluid rather than a gas, a greater thermal load can be repeatedly extracted from the tissue under controlled physiologic conditions using a liquid beyond the thermal load which may be extracted using a compressed gas. In addition, the pressure associated with release of a compressed gas into an excluded space may potentially damage tissue and may be difficult to control with respect to pressure and temperature. A fluid lavage, on the other hand, may be controlled based on temperature and pressure to provide a repeatable effect on the target organ. Compressed gas or other rapid cooling mechanisms, though, may be utilized in combination with this therapy in order to chill a solution to subzero temperatures after introduction into the body. In this variation, the biocompatible fluid capable of retaining fluid characteristics in a subzero state, or "anti-freeze solution", may be infused into the lumen or cavity after which the cooling probe may be introduced. Heat may be drawn from the anti-freeze solution until the desired hypothermic ablation temperature has been achieved for the desired duration of time. Fluid may or may not be circulated during this process via a pump or agitating element within the catheter in order to improve distribution of the ablative fluid.

In yet another variation, the treatment fluid may function to expand the uterus for consistent ablation, function to distribute the cryoablative freezing more evenly throughout the uterus, and potentially function to prevent ice formation at the surface of the lumen or body cavity. In the uterus, for example, this layer of ice that may form on the surface of the endometrium is highly insulating and may prevent transmission of the cryoablative freeze zone to deeper surfaces requiring a longer treatment with potentially erratic effects. The apparatus may be used with, for example, lipophilic, hydrophilic or amphipathic solutions with the latter two being having the ability to remove any aqueous fluid from the surface of the target cavity or lumen which may interfere with conduction of the heat from the target tissues into the cryoablative fluid.

Additionally and/or alternatively, the apparatus and methods described herein may be used as an adjunct to other treatments, such as the Her Option® therapy (American Medical Systems, Minnetonka, Minn.), by utilizing a lavage of the target cavity or lumen such as the uterus with the aqueous anti-freeze solution either prior to or during treatment in order to provide superior transmission of cryoablation with other existing cryoprobes without creation of the insulating ice layer at the surface. Moreover, lavage of the target lumen or cavity with a biocompatible antifreeze solution may be performed to improve transmission of the cryoablative effect as an adjunct to any cryotherapy treatment anywhere in the body where applicable. As described herein, the cryoablative fluid may also be introduced and/or lavaged within the target lumen or body cavity within a balloon which may be expanded to contact the walls of the lumen or body cavity. The cryoablative treatment fluid may be actively lavaged in and out of the balloon and/or deeply chilled by a cryoprobe within the balloon after introduction into the body cavity or lumen. Moreover, the anti-freeze solution may also comprise various salts and/or other biocompatible molecules capable of driving the freezing temperature of the solution below, e.g., −10 degrees Celsius. Additionally, the fluid may be capable of resisting freezing even at a temperature of, e.g., −50 degrees Celsius. A combination of salts, alcohols, glycols and/or other molecules may be used to provide this resistance to freezing in an aqueous solution.

In yet another variation, a cryoprobe with, e.g., a protective cage and/or a recirculator/fluid agitator, may be utilized to ensure that the hypothermic fluid is evenly distributed. The cage may be configured into various forms so long as it exposes the fluid to the surface of the cryoprobe while preventing direct contact of the cryoprobe with the wall of the lumen or cavity to be ablated (such as a uterus). A recirculator may comprise, e.g., a stirring element at the tip of the cryoprobe, an intermittent or continuous flow system or other fluid movement mechanism.

BRIEF DESCRIPTION OF THE DRAWINGS

For the purposes of the drawings and preferred embodiments, application to the esophagus will be shown. However, the apparatus and methods may be applied to any body cavity/lumen which may be visualized with an endoscope or other visualization mechanism.

FIGS. 12A and 12B shows another example of a single balloon device for ablation treatment within the uterus and/or endometrial lining.

DETAILED DESCRIPTION OF THE INVENTION

Figure 1:
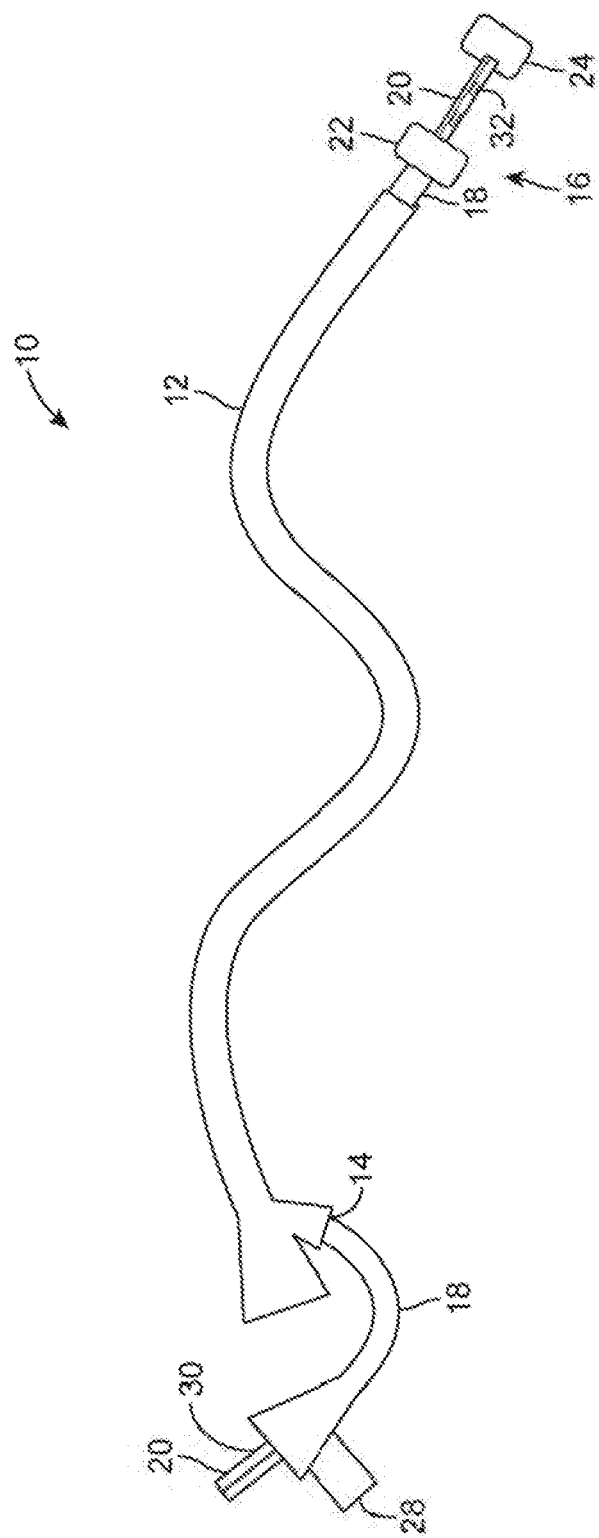
FIG. 1 shows an example of a device advanced through an endoscope, e.g., a nasally or orally inserted scope.

FIG. 1 shows a perspective view of one example of the treatment assembly 10 positioned within a working channel 14 of an endoscope 12 (e.g., orally or nasally insertable scope). In this example, the treatment device 16 itself may utilize a first catheter 18 having an inflatable or expandable balloon member 22 and a second catheter 20 that may slide freely with respect to the first catheter 18 and also having an inflatable balloon member 24 at its distal end. The first catheter 18 as well as second catheter 20 may have a fluid and/or gas tight seal 30 formed at the proximal end of the catheters. The inflatable and/or expandable members 22, 24 (shown in this example as inflated balloons) may be pressurized to effectively and safely occlude the lumen. The balloons may be filled with chilled or room temperature fluid to prevent possible damage caused by balloon rupture or seepage around the balloon. Pressure within the inflatable or expandable balloon members may also be monitored to ensure that a tight seal has been formed within the lumen or body cavity.

Additionally, the fluid may be introduced into the treatment area through a fluid and/or gas port 28 and into the lumen of the catheter which terminates with the proximal balloon 22 and leaves the catheter through perforations or holes 32 within the second catheter 20 which terminates in the distal balloon 24, although this flow path may easily be reversed if necessary. Alternatively, one or more ports can be designed into the lumen between the distal 24 and proximal 22 balloons, such that the heated or cooling fluid exits one or more ports 32 in the lumens near the distal balloon 24, and is then evacuated in a port or ports designed within the lumen of the first catheter 18 nearest the proximal balloon 22. In this variation, the endoscope 12 may insulate the catheters allowing the catheters to be much smaller than would be otherwise possible and allowing it to fit within the working channel 14 of a standard endoscope 12. One or more pressure sensors may be used to detect both inflation pressures of the balloons and/or the pressure seen by the body cavity/lumen that is exposed to the treatment fluid/vapor. In the manner, fluid/vapor flow may be controlled by the pressure sensing elements within the body cavity/lumen to ensure that safe pressures are never exceeded. Manual controls may be used for creation and/or maintenance of these pressures (e.g. syringes with stopcocks) or automated and/or semi-automated systems can be used as well (e.g. pumps with PID loops and pressure sensing interconnectivity. Although the fluid and/or gas for tissue treatment may be heated or chilled prior to introduction into the treatment area in contact with the tissue, the fluid and/or gas may alternatively be heated or chilled after introduction into the treatment area and already in contact with the tissue.

Figure 2:
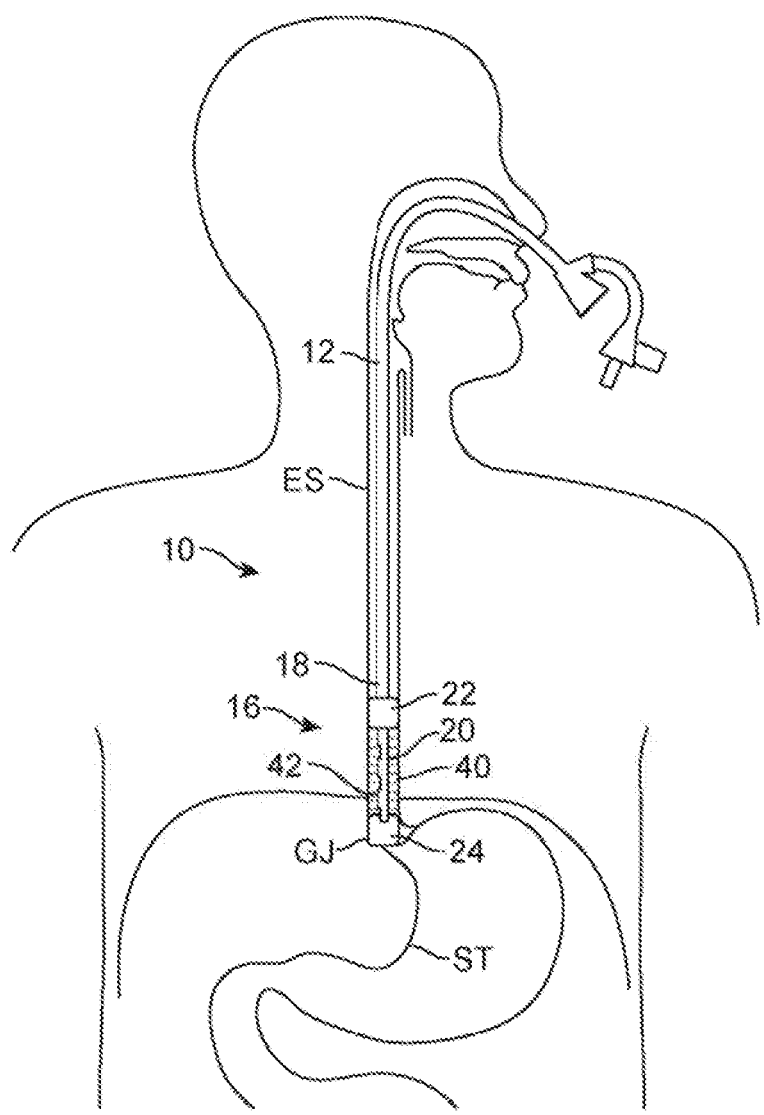
FIG. 2 shows an example of a device advanced through the working channel of nasal endoscope.

FIG. 2 shows an example where the second catheter 20 and distal balloon member 24 is slidable relative to the proximal balloon 22. This examples illustrates the endoscope inserted through the nasal cavity and advanced through the esophagus ES where the catheters 18, 20 may comprise single or multi-lumen catheters having inflation lumens for the distal 24 and proximal 22 inflatable/expandable elements, infusion port and extraction port. At least one of the catheters may be fitted with either a pressure transducer 42 or a lumen to carry the pressure signal from the treatment area back to the controller or dial gauge. Pressure sensing may be accomplished through a small, air capsule proximal to the distal balloon 24, but within the treatment area. Both of the balloons 22, 24 may be inflated along the esophagus ES in the proximity to the gastroesophageal junction GJ proximal to the stomach ST to create a treatment space 40 which encompasses the tissue region to be treated.

In an alternative embodiment, an extraction lumen may be omitted as a preset dose of heated fluid and/or gas may be delivered, allowed to dwell and then either extracted through the same lumen or rendered harmless with the infusion of cold fluid. This treatment algorithm would provide an even simpler therapy and would rely on the exclusion of a certain area and exposure of that area to a fluid or vapor with the desired energy. Infusion of the fluid or vapor may be controlled to ensure that the treatment area is not exposed to excessive temperatures.

Figure 3:
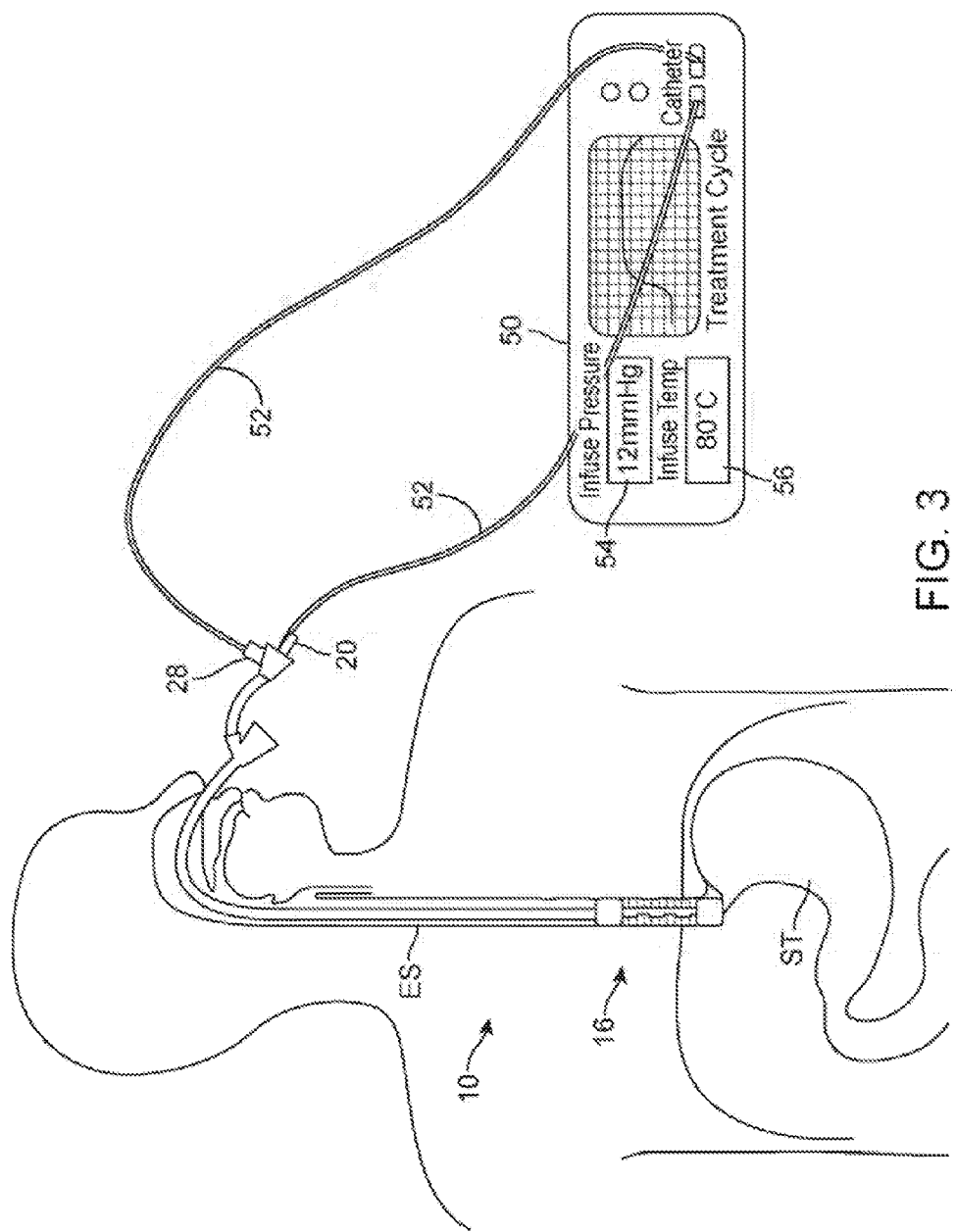
FIG. 3 shows an example of a device attached to a logic controller.

FIG. 3 shows another example where the treatment assembly 10 may be in communication with a controller 50, such as a logic controller. Controller 50 may control certain parameters such as infusion pressure 54 of the fluid as well as fluid temperature 56 and it may be coupled to the assembly by one or more cables 52. The pressure in the treatment area, the elapsed time, the temperature of the fluid, and the extraction rate may also be monitored and controlled.

Figure 4:
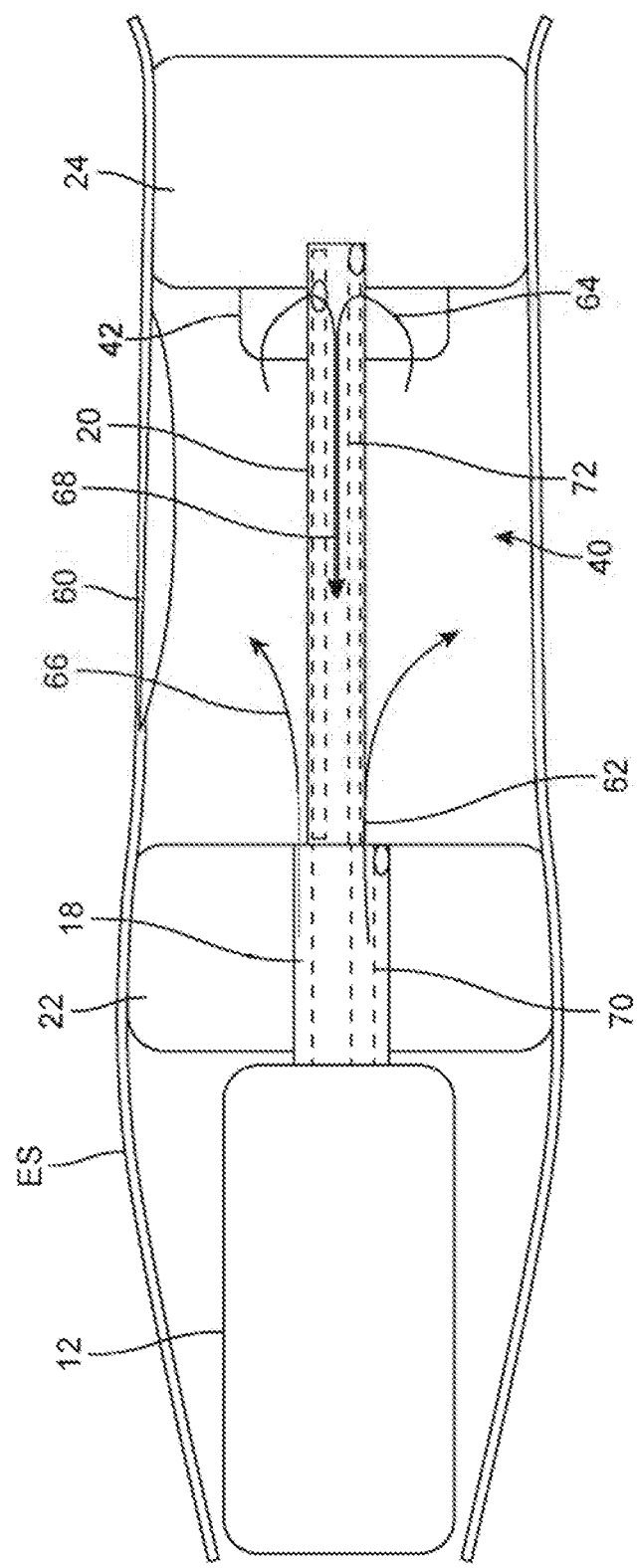
FIG. 4 shows an example of a device placed through working channel of nasal endoscope and deployed within an esophagus for treatment.

FIG. 4 shows a detail view of the treatment area 40 defined, in this case, by two balloons 22, 24. The first catheter 18 may open into the lumen just after the proximal balloon 22 and this catheter 18 may be inserted along with or prior to insertion of the second catheter 20. The first catheter 18 internal diameter is greater than the outer diameter of the second catheter allowing for fluid (and/or vapor) to be infused or extracted around the outer diameter of the second catheter 20. The second catheter 20 a first lumen for balloon inflation and a second lumen for evacuating the treatment region 40. With the balloons inflated into contact against the esophagus ES, the treatment area 40 may encompass the tissue region to be treated, e.g., a lesion 60 such as Barrett's esophagus or esophageal cancer lesion and the distal end of the endoscope 12 may be positioned into close proximity to proximal balloon 22 and the treating fluid and/or gas 66 may be infused through the annular lumen 70 defined through first catheter 18 and between second catheter 20 such that the fluid 66 may enter through opening 62 into the treatment region 40 while contained by the balloons. Once treatment has been completed, the fluid may be evacuated 68 through one or more openings 64 located along the second catheter 20 proximal to distal balloon 24 and proximally through the second catheter 20 through the evacuation lumen 72. As previously mentioned, a pressure sensor 42 (e.g., pressure measuring air capsule) may be positioned along either the first 18 and/or second 20 catheter for sensing the various parameters. Additionally, the treatment fluid and/or gas may include any number of fluids, vapors, or other chemically active (e.g., chemotherapeutic) or inactive compounds for additional treatments to the tissue.

In the event that the treatment is provided by a simple timed dwell, the extraction 72 and infusion 70 lumens may not both be utilized. The pressure sensing element 42 (solid-state, piezoelectric, or other method) may be located on either the first or second catheters and the second catheter and may comprise a simple slidable balloon. A pressure sensor for the treatment may omitted so long as the pressure can be controlled by other mechanisms, e.g., a check valve or a simple gravity fluid column. An active pressure measurement, though, may ensure that safe pressures are not being exceeded.

The second catheter 20 may fit easily within the first catheter 18 and may be slid inside the first catheter 18 until its distal balloon 24 is distal to the first balloon 22. The distal balloon 24 may then be inflated just beyond the distal portion of the treatment area 40 and the endoscope 12 may be pulled back. The most proximal extent of the lesion 60 may then be identified and the proximal balloon 22 may be inflated proximal to this area. Once the treatment area 40 has been enclosed (which may be verified by infusing fluid 66 and/or vapor under visualization and observing the seal around the balloon, balloons and/or expandable member) the lumen or body cavity may then be filled with the treatment fluid and/or vapor to a safe pressure. The fluid and/or vapor may also contain active agents (e.g. chemotherapeutic and/or anesthetic agents) and comprise more than simply an inactive fluid and/or vapor. Options would be for the active agents to be delivered prior to, during and/or post treatment of the heating (or cooling) fluid and/or vapor.

As the treatment assembly 16 does not contain the treatment fluid or vapor within a balloon(s) or expandable member and allows it to freely flow over the treatment area, the therapy may be applied consistently leaving no areas left untreated (as is frequently seen with balloon infusion-based or RF therapies). Additionally, treatment may be accomplished with a heated fluid (rather than a high energy electrode or excessively hot vapor) or a more controlled treatment can be achieved through the use of a relatively cooler fluid with a longer treatment time. In addition, the esophagus ES is a fluid transport type organ (lumen) and may be more compatible to fluid based therapies than with RF-based therapies. It is also believed that the safety margin of such treatments may be better than with an RF-based therapy.

Figure 5:
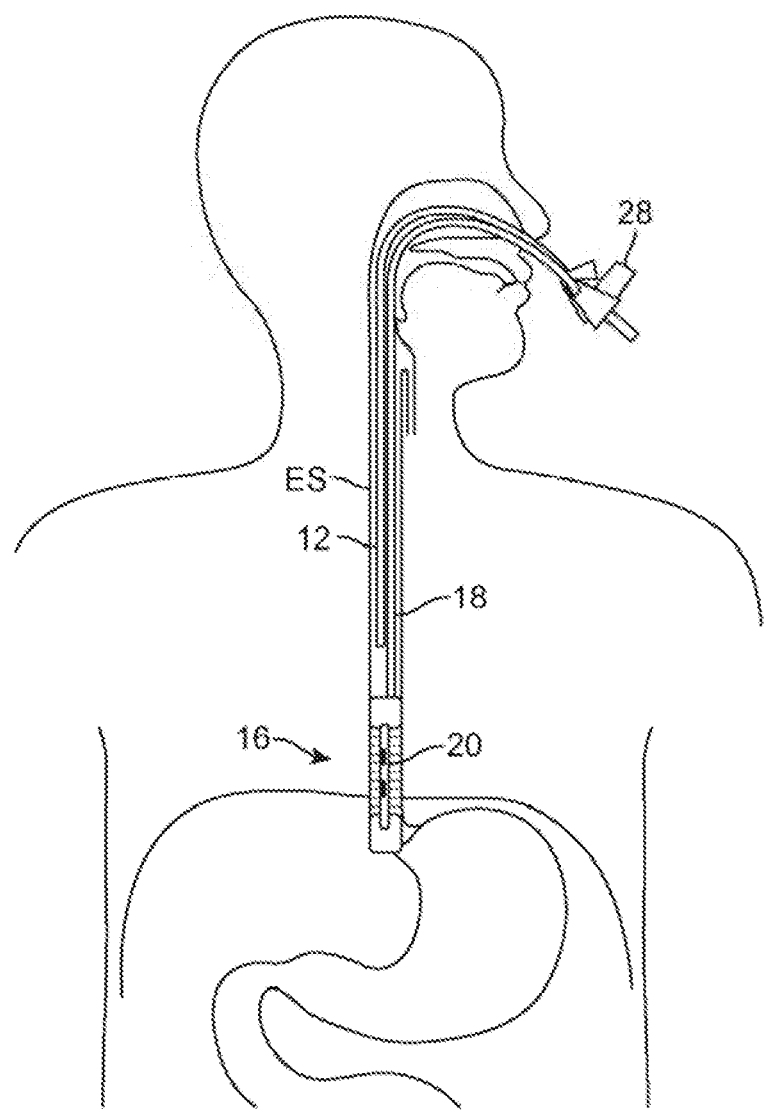
FIG. 5 shows an example of a device advanced alongside an endoscope.

FIG. 5 shows an alternative embodiment of the device in which the first catheter 18 and second catheter 20 of the treatment assembly 16 may be inserted alongside an endoscope 12 which may be used to provide for visualization. Due to the small size of the catheters, this embodiment is feasible.

Figure 6C:
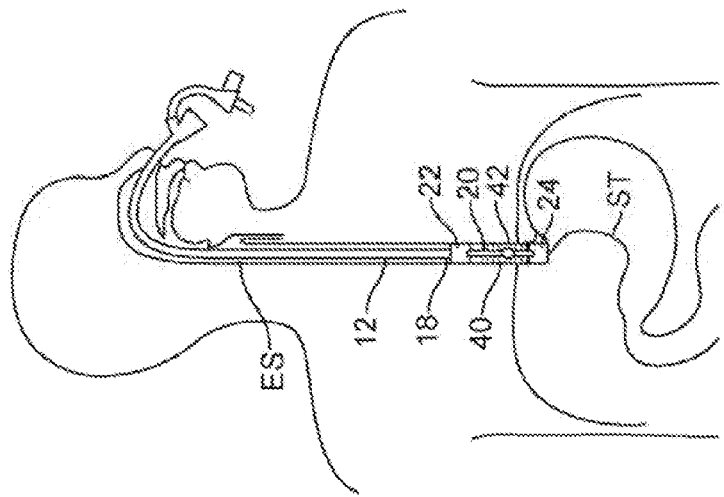
FIGS. 6A to 6C show a device being introduced through an endoscope and deployed for treatment within the esophagus.
Figure 6B:
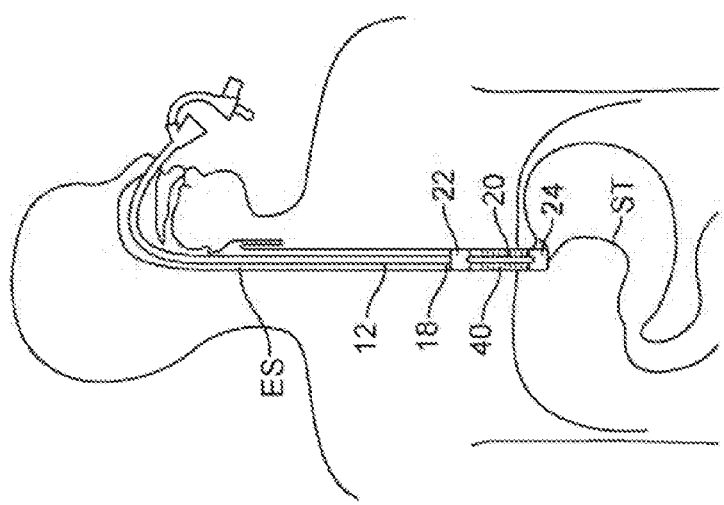
Figure 6A:
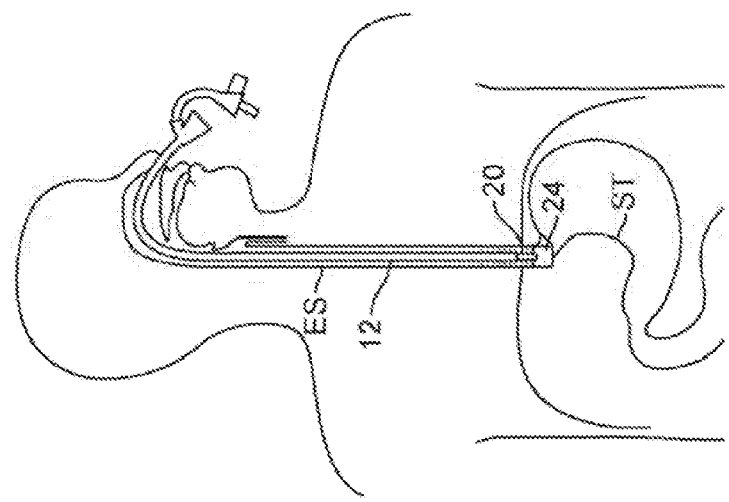

FIGS. 6A to 6C illustrate an example for a placement procedure for the assembly for the treatment of a body lumen such as the esophagus ES. The catheters may be inserted simultaneously or separately through the working channel of the endoscope 12. In one example, the larger first catheter 18 may be inserted first followed by insertion of the second catheter 20 within the lumen of the first catheter 18. Once both single or multi-lumen balloon catheters have been inserted and after the endoscope 12 has been advanced through the esophagus ES and into proximity to the tissue treatment region, the distal balloon 24 may be advanced to define the distal end of the treatment area and inflated (e.g., with chilled, room or body temperature fluid) while under visualization through the endoscope 12, as shown in FIG. 6A. The endoscope 12 may then be pulled back until the proximal end of the desired treatment area has been identified and the proximal balloon 22 may be slid over the shaft of the second catheter 20 and inflated (e.g., with chilled, room or body temperature fluid) at a site just proximal to the most proximal portion of the lesion, as shown in FIG. 6B.

With the treatment area 40 now enclosed by these balloons, an optional pressure capsule 42 (e.g., solid state, piezoelectric or other pressure sensing method) may be inflated and the treatment may proceed, as shown in FIG. 6C. The treatment session then exposes the lumen or body cavity to fluid pressurized to a positive pressure in the range of, e.g., 5-100 cmH2O (although this pressure may be maintained at a level below an inflation pressure of the inflation balloons) at temperatures between, e.g., 50 and 100 degrees Celsius, for a period of, e.g., 1 second to 10 minutes. Additionally and/or alternatively, the treatment area 40 may be lavaged for a period of time with an anesthetic (e.g., lidocaine or bupivicaine) to reduce pain with the procedure prior to the application of thermal energy or other active compounds. Accordingly, ablation may be accomplished at a consistent depth of, e.g., about 0.5 mm, throughout the esophagus ES.

Figure 7C:
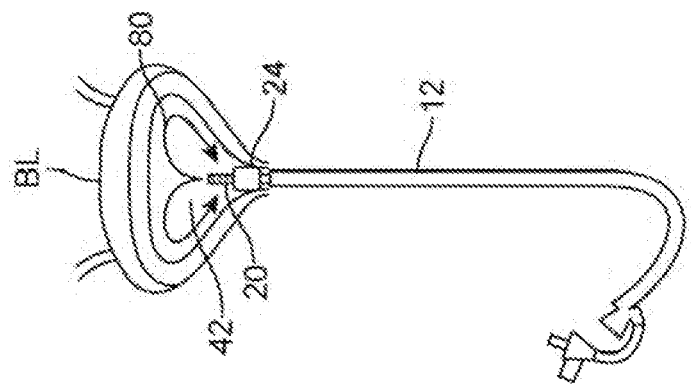
FIGS. 7A to 7C show examples of a device introduced through an endoscope for insertion within a bladder.
Figure 7B:
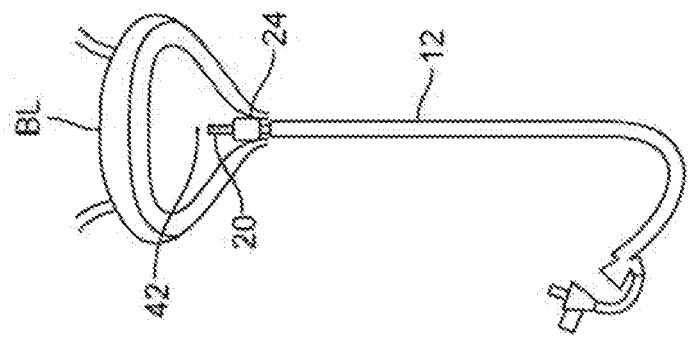
Figure 7A:
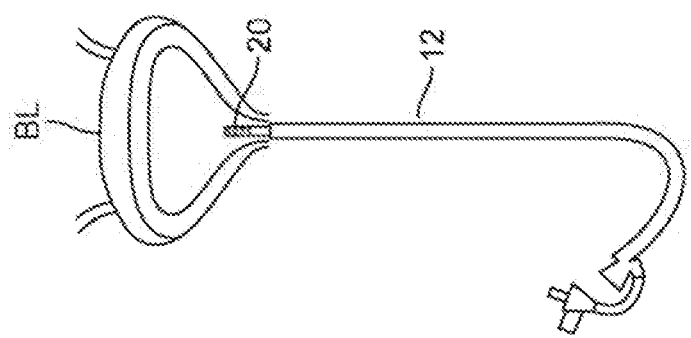

FIGS. 7A to 7C illustrate another example for treatment of an enclosed body cavity (shown here as a bladder BL). In this example, a single balloon may be used to effect infusion and extraction of the treatment fluid. Pressure may be monitored to ensure that the therapy is safe and a relatively lower temperature fluid may be used (e.g., 42-100 C) so that the entire cavity may see a controlled, uniform thermal load. The order or catheter placement may vary as may the sequence for balloon inflation or exposure to active or inactive fluid or vapors in this or any embodiment of the device. As shown in FIG. 7A, an endoscope (or cystoscope) 12 may be inserted into the target organ BL then fluid catheter 20 may be advanced into the lumen. With the endoscope 12 inserted and occlusion balloon inflated 24 (e.g., with unheated fluid) to seal the organ, a pressure sensor 42 may also be optionally inflated to measure pressure, as shown in FIG. 7B. Optionally, an anesthetic or pre-treatment medication may be delivered into the bladder BL, if so desired. Then, a high or low temperature fluid 80 may be circulated within the bladder BL under pressure adequate to safely distend the organ to ensure complete treatment, as shown in FIG. 7C.

Figure 8C:
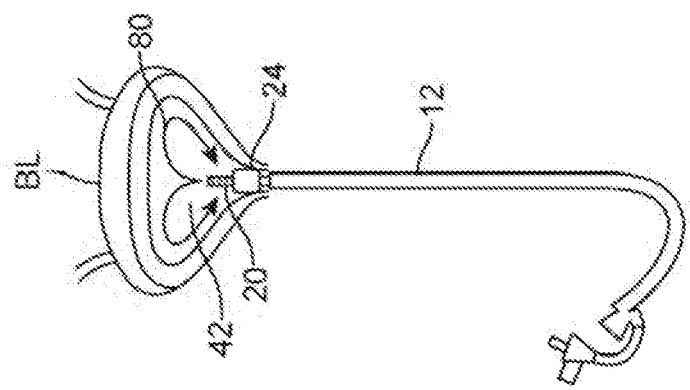
FIGS. 8A to 8C show examples of a device preparing the treatment area with a pre-treatment lavage prior to treatment.
Figure 8B:
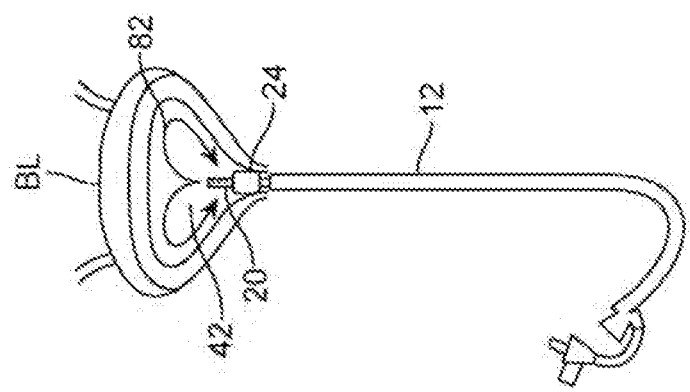
Figure 8A:
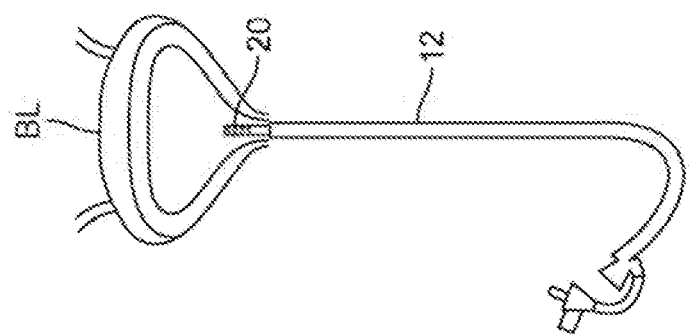

FIGS. 8A to 8C illustrate another example for treatment where the use a fluid lavage to prepare the treatment area (here shown as the bladder BL) may be accomplished prior to application of thermal (or cooling) energy and/or active compounds. As previously described, the endoscope 12 and catheter 20 may be introduced into the bladder BL and subsequently sealed with the occlusion balloon 24, as shown in FIGS. 8A and 8B. Preparation of the treatment area may involve use of an anesthetic to decrease pain during therapy or the use of an arterial constrictor to reduce blood flow to the organ or lumen. Alternatively, other pre-treatment fluids 82 may include, e.g., anesthetic, vascular constrictor, chilled fluid, active component antidote, etc. The pre-treatment fluid 82 may be evacuated (or left within the bladder BL) and the lavage with the treatment fluid 80 may be introduced into the bladder BL for treatment, as shown in FIG. 8C.

Alternatively, the pre-treatment fluid 82 may also be chilled (or heated) to cool (or warm) the lumen or organ prior to treatment so that the thermal (or cooling) energy may be applied to the internal surface of the lumen or body cavity with minimal transmission or conduction of the elevated (or cooling) temperatures to the submucosal tissues (or tissues lining the body organ or lumen). Utilizing the pre-treatment of the area may avoid damage to the underlying tissues to thereby avoid many of the complications of therapy. For example, strictures and/or stenosis (or tightening) of the tissue can be avoided by controlling the depth of penetration which may be controlled by pre-treating the area with a chilled fluid so that the submucosa can absorb significant amounts of heat without reaching damaging temperatures.

The depth of penetration may also be controlled through the use of a lower temperature fluid for thermal ablation so that the submucosa can cool itself with its robust vascular circulation (which is less robust in the mucosa and epithelium). In the event that an active compound is used, as well, an antidote to this compound may be delivered to the patient (either systemically or as a local pre-treatment) so that the underlying tissues and submucosa are not damaged. One example of this is the use of powerful antioxidants (systemically or locally) prior to lavage of the esophagus with, e.g., methotrexate. The methotrexate may have a powerful effect on the tissues to which it is directly exposed in the lumen or body cavity, but the anti-oxidants may prevent deeper penetration of the methotrexate. The neutralizing compound may also be placed within the balloon or in the lumen of surrounding lumens or body cavities to prevent exposure of these areas in the event of balloon rupture.

Figure 9:
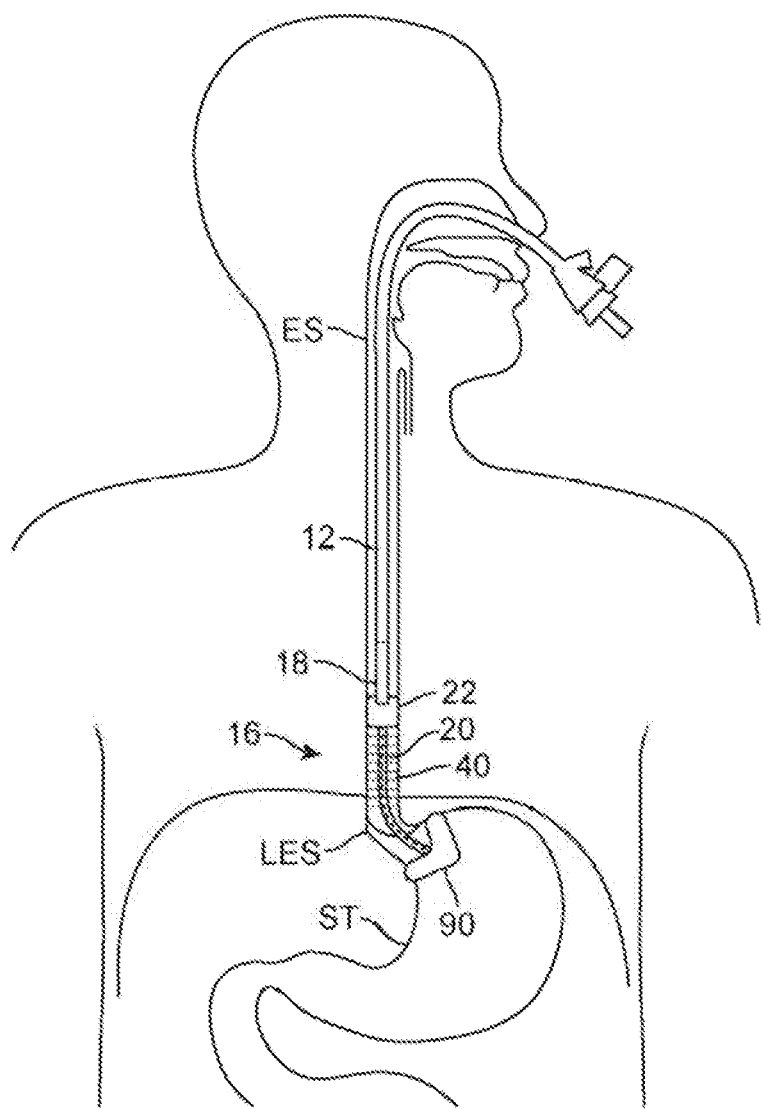
FIG. 9 shows an example of a distal occlude having an umbrella-like shape deployed in proximity to a gastroesophageal junction for treatment.

FIG. 9 shows another example where the distal occlusion member may be configured into an umbrella-like element 90 which may be expanded in the stomach ST and placed over a tissue region which is typically difficult to occlude by a balloon. For instance, such a shape may allow for ablation of the lower esophageal sphincter LES at the gastroesophageal junction (or other sphincter region if used elsewhere). The expandable, umbrella-like structure 90 may form a firm seal at this site while allowing the ablation fluid (hot or cold) to contact the entire gastroesophageal junction. Once expanded, the umbrella-like element 90 maybe held firmly against the stomach ST by traction on the endoscope 12 or by a tensioning element on the catheter and balloon itself.

In addition, this element 90 may optionally incorporate a biased or spring-loaded element or other external force mechanism to provide steady pressure and a firm seal against the stomach lining. Alternative structures may also incorporate a more complex, nitinol cage (or other rigid material) connected by a thin, water-tight film. For example, nitinol may be used to decrease the overall profile of the obstruction element and increase its strength and durability.

Figure 10:
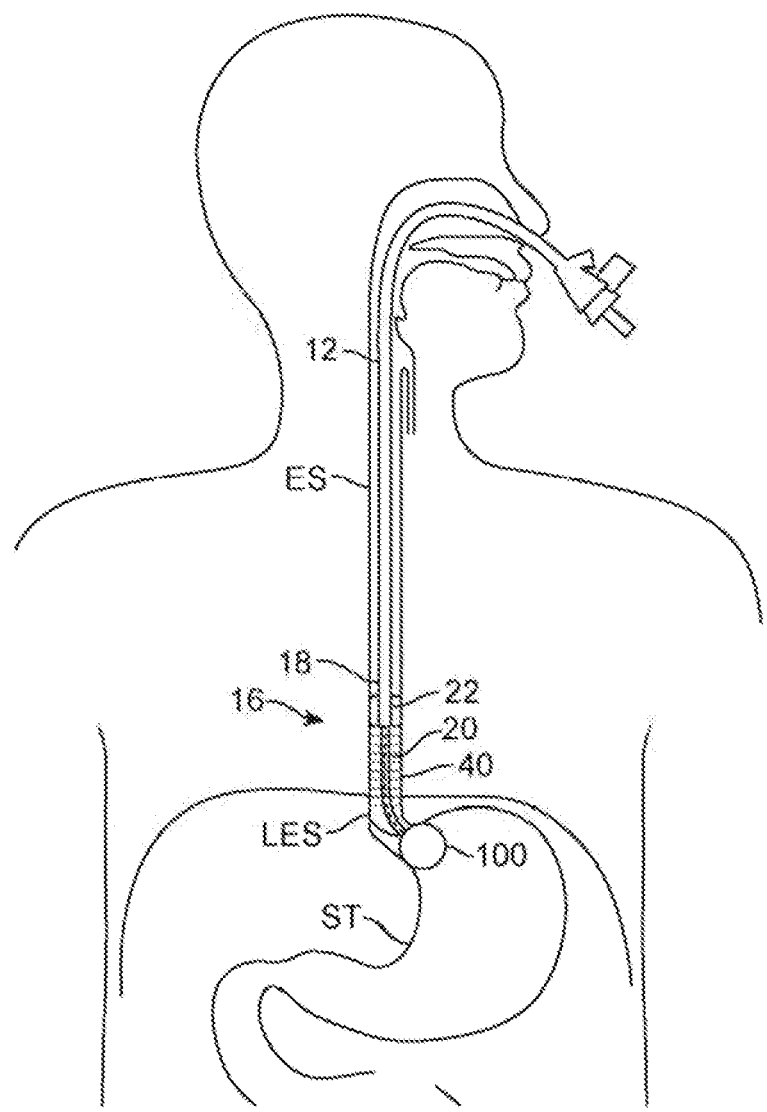
FIG. 10 shows another example of an endoscopic balloon sheath having a distal occluder expanded distal to gastroesophageal junction for treatment.

FIG. 10 shows another example which utilizes an endoscopic balloon sheath utilized as a distal occluder allowing for exposure and treatment of the distal gastroesophageal junction. In this embodiment, the second catheter 20 may have a distal occlusion balloon 100 which may be passed through the working channel of the endoscope 12 or through a channel incorporated into the balloon sheath itself (outside of the actual endoscope). Once expanded into an enlarged shape, the balloon 100 may be retracted to fit entirely over the lower esophageal junction LES to form the distal seal by traction on the endoscope 12 or by a tensioning element on the catheter and balloon itself. This gastric occlusion balloon may allow for exposure of the gastroesophageal junction while preventing fluid flow into the stomach ST. The balloon 22 may be configured to be saddle-shaped, circular, wedge-shaped, etc. It may also be self-expanding and non-inflatable.

Additionally, the proximal balloon 22 may be configured to be part of sheath that is placed over the tip of the endoscope 12 or it may be formed directly upon the endoscope tip itself. An inflation lumen may run inside the endoscope 12 or it may run alongside the endoscope 12 in a sheath or catheter. The balloon sheath may also incorporate a temperature sensor, pressure sensor, etc. Moreover, the proximal occlusion balloon 22 may optionally incorporate a temperature or pressure sensing element for the therapy and it may be positioned either through the working channel(s) of the endoscope 12 or alongside the endoscope 12 within the endoscopic balloon sheath.

In yet another embodiment, in order to reduce the risks associated with fluid flow and lavage, a fluid or gel may be infused into the esophagus between the balloons then heated or frozen in situ in order to provide the desired ablative effect without circulating any fluid or gel. In one example of this configuration, a gel may be infused into the esophagus and pressurized to a safe level (e.g., 30-100 mmHg) which may be then rapidly chilled using, for example, a compressed gas and/or a Peltier junction-type cooling element. The gel may freeze at a temperature below that of water and allow for rapid transmission of the ablative temperature to the tissues being treated. This gel may also be a liquid with a freezing point below that of water in which case the treatment zone may be lavaged with this fluid prior to treatment to remove free water and prevent crystal formation during therapy. Once the therapy has been completed, the gel or liquid may be removed or left in the esophagus to be passed into the stomach. In the event that a Peltier cooling or heating element is used, the polarity may be reversed once therapy is complete in order to reverse the temperature and terminate the ablation session.

The distance from the lower end of the distal most portion of the catheter can be on the order of about 150 mm. The distance between the proximal and distal balloons are adjustable by the operator but can be adjusted, e.g., from as small as 0 mm to as large as 25 cm. The treatment zone may have a range of, e.g., 3 to 15 cm.

In yet an additional embodiment, an energy generator (e.g., a RF electrode or hot wire or other energy source) may be advanced into the treatment area in a protective sheath (to prevent direct contact with body tissues) and energy may be applied to the treatment fluid to heat it to the desired temperature. Once the fluid is adequately heated and enough time has passed to achieve a controlled ablation, the fluid may then be evacuated or neutralized with the influx of colder fluid. This embodiment would allow for a very low-profile design and would not require any fluid heating element outside of the body.

In another variation, the cavity or lumen may be exposed to the hot water at a temperature of less than, e.g., 100 degrees Celsius, but greater than, e.g., 42 degrees Celsius, to allow for easier control of the treatment due a longer treatment period. Ranges for optimal hyperthermic treatment include temperatures between, e.g., 42 and 100 C and exposure periods ranging from, e.g., 15 seconds to 15 minutes. In this embodiment, treatment may be effected with an active (e.g., Methotrexate) or inactive fluid at a temperature of, e.g., 90 degrees C., for a period of, e.g., 5-60 seconds, depending on the depth of penetration desired.

Figure 11:
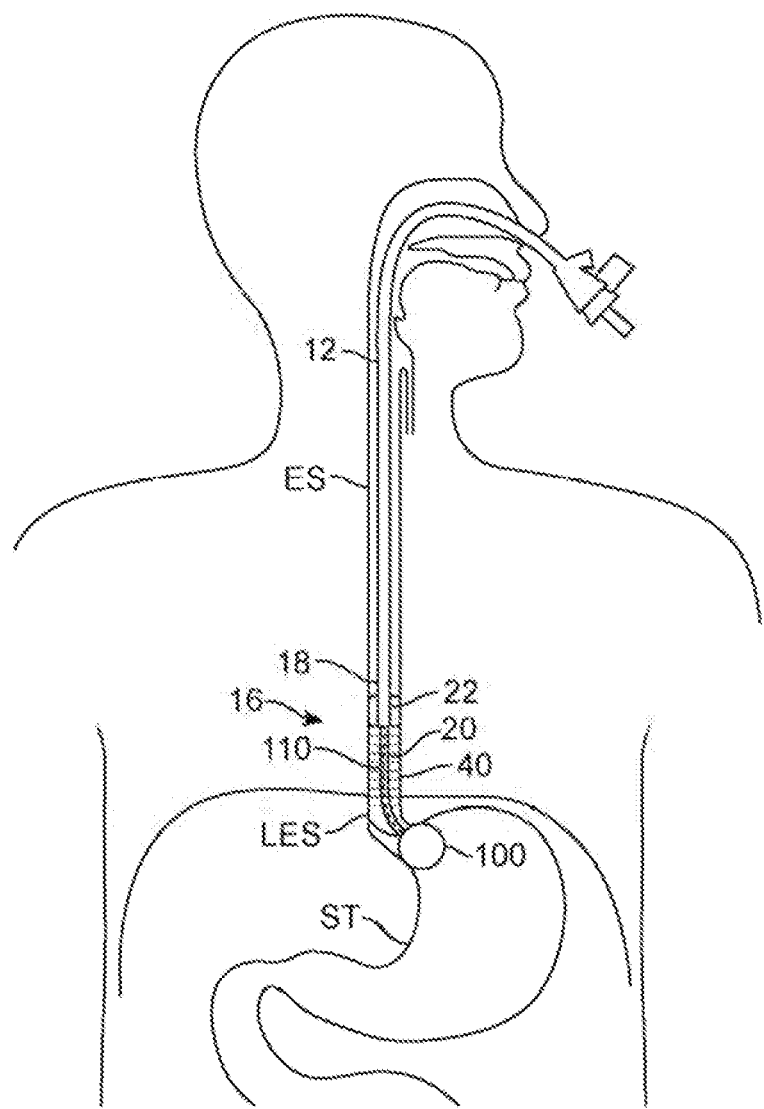
FIG. 11 shows another example where the treatment fluid is introduced between the deployed balloons for treatment.

FIG. 11 shows another example of an endoscopic balloon sheath which may be used to provide proximal occlusion of the treatment area 40 and may house one or more of the temperature and pressure sensors. This variation may incorporate a stirring/agitating or recirculation mechanism 110 incorporated into the device which may actuated within the treatment area 40 once the treatment fluid has been introduced to allow for even cooling/heating. The distal occlusion balloon 100 may be inflated within the stomach ST and pulled proximally with controlled traction against the gastric portion of the lower esophageal sphincter LES, as previously described.

In this example, a chilled fluid lavage (or vapor infusion) may then be initiated and the tissue ablated via freezing. A pre-treatment lavage, e.g., a hypertonic, hyperosmotic saline solution, may be introduced with above freezing temperatures followed by a sub-zero temperature lavage to ablate the tissues within the treatment area 40. The hypertonic, hyperosmotic fluid may achieve temperatures down to, e.g., −40 degrees C., without creating ice crystals in the treatment area 40 due to the pre-treatment lavage removing any free water. The treatment fluid following the pre-treatment lavage may have temperatures of, e.g., −2 degrees C. to −40 degrees C., for ablation or more particularly a temperature range of, e.g., −5 degrees C. to −20 degrees C. This temperature range may allow for freezing and crystal formation in the exposed tissues without damaging the underlying submucosa (which is protected by the circulation of body temperature blood that prevents freezing). This temperature range can also be easily achieved with hypersalination of aqueous fluid using sodium chloride and may inhibit any undesired damage to tissues with brief contact. Also, the use of a heavily salinated or other sub-zero solution lavage may provide optimal sealing of the occluding balloons in that any sub-zero temperatures outside of the pre-lavaged treatment zone may form an impaction of ice crystals and prevent any further fluid flow outside of the treatment zone. This hypersalinated water solution is but one freezing solution, though, and any aqueous or non-aqueous fluid or vapor that can be infused and extracted at this temperature could be used. Alternatively, cryoablative fluid can simply be formed by cooling ethanol or another aqueous or lipophilic fluid with subzero cooling temps with compressed gas or dry ice. In another alternative, compressed $CO_2$ or dry ice may be introduced into the fluid (e.g., ethanol, butylenes glycol, propylene glycol, etc) to cool it to, e.g., −50 degrees C. or below.

The use of a subzero solution within this range may also allow for fine control of the treatment depth as tissue damage would not begin to occur until a temperature differential of about 37 degrees C. is achieved (assuming a body temperature of 37° C.), but once this threshold is reached tissue damage occurs rapidly due to ice crystal formation. In contrast, tissue damage is on a continuous spectrum with hyperthermia and damage may begin to occur at a temperature differential of, e.g., 5 degrees C. Thus, the ability of the vasculature to protect the underlying tissues from damage is greatly reduced due to the small difference between the temperature of protective blood versus the temperature of the ablating fluid. With hypothermic lavage, the protective blood may differ by, e.g., 37 degrees C., in temperature and may thus allow for control of ablation depth based on the temperature of the fluid lavage and the time of exposure.

Although illustrated esophageal therapy, this therapy could be used in any body cavity/lumen for therapeutic purposes including, but not limited to, gastrointestinal therapy, stomal tightening (e.g., post bariatric surgery), urogynecologic uses (treatment of cervical pre-cancers or cancers, endometrial lining treatment, stress incontinence therapy), prostate therapy, intravascular therapy (e.g., varicose veins) or treatment of any other body cavity/lumen. In the event that an entire body cavity is being treated (e.g., the entire uterus) a single balloon system may suffice to exclude the entire cavity. The fluid cycling or dwell may then be accomplished with use of a pressure-controlled exposure of the cavity or lumen.

FIGS. 12A and 12B show another example of how the system may be introduced into, e.g., a uterus UT, through the cervix for treatment via the lavage catheter 20. In this example, the catheter 20 may have a diameter of about, e.g., 8 mm, or in other examples, a diameter of about, e.g., less than 6 mm Infusion of the lavage fluid may fully distend or partially distend the uterine walls. Optionally, catheter 20 may incorporate a tip 120 to perform one or more functions including, e.g., an expandable cage or scaffold to prevent direct exposure of a cryoprobe to the tissue walls of the uterus UT, an agitator or recirculator to ensure even distribution of cryoablation effect, etc. As previously described, the system may be used with lavage or with infusion then cryoprobe chilling of fluid. In an alternate embodiment, infusion of an antifreeze fluid and insertion of the cryoprobe may be done separately with chilling of the anti-freeze done after the cryoprobe insertion.

In this and other examples, the therapy may be guided by time/temperature tracking or visualization (e.g., hysteroscope, endoscope, ultrasound, etc.). Pressure may be regulated by a pressure sensor in line with the infusion or extraction lumen or a dedicated pressure lumen in a multi-lumen catheter. Additionally, pressure may also be regulated by limiting infusion pressure (e.g., height of infusion bag, maximum pressure of infusion pump, etc.). Any organ, body cavity or lumen may be treated using the described lavage and/or infusion/cryoprobe technique described here for the uterus.

In yet another example, the system may employ a thermally conductive fluid having a thermal conductivity greater than that of saline. This thermal conductivity may help to ensure that the fluid within the body cavity or lumen is at the same temperature throughout even without agitation or lavage. Such a fluid may be used with the fluid lavage and/or the fluid infusion followed by application of a cryoprobe. The improved thermal conductivity may be achieved via a variety of different options including, but not limited to, choice of a thermally conductive fluid or gel, addition of thermally conductive compounds to the fluid or gel (e.g., metals or metal ions, etc.) and/or agitation of the fluid within the cavity to help achieve equilibration of the temperature.

Additionally, the fluid may be infused as a fluid or gel until a set pressure is achieved. The cryoprobe may then be introduced into the body cavity/lumen and heat may be withdrawn from the fluid/gel. Prior to or in concert with the achievement of a cryotherapeutic (ablative or non-ablative) temperature, the fluid or may form a gel or solid. This may be utilized such that fluid or gel within the cavity may be trapped within the target lumen or body cavity with its change in viscosity or state thereby preventing leakage of the fluid or gel and unwanted exposure of adjacent tissues to the cryotherapeutic effect. Due to the higher thermal conductivity or the gelled or frozen fluid or gel, the continued removal of heat from the gelled or frozen mass may be rapidly and uniformly distributed throughout the body cavity or lumen. The solution may also be partially frozen or gelled and then agitated or recirculated to ensure even greater distribution of the cryotherapeutic effect. Furthermore, the fluid or gel may be made thermally conductive by addition or a biocompatible metal o metallic ion. Any metal or conductive material may be used for this purpose such as silver, gold, platinum, titanium, stainless steel, or other biocompatible metals.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A method for treating a body cavity or lumen, comprising:
   positioning a tissue region of interest between a distal occlusion member and a proximal occlusion member which are adjustably movable relative to one another via adjustment of a catheter;
   occluding the tissue region to be treated between the occlusion members such that a treatment area is defined therebetween;
   introducing a hyperthermic or hypothermic fluid and/or gas into the treatment area such that the tissue region is treated by thermal ablation with the hyperthermic or hypothermic fluid and/or gas contacting the tissue region;
   monitoring a first pressure of the hyperthermic or hypothermic fluid and/or was introduced into the treatment area;
   comparing the first pressure against a second pressure within the occlusion members; and
   adjusting the first pressure to be below the second pressure if the first pressure exceeds the second pressure.

2. The method of claim 1 wherein positioning comprises positioning the catheter within a body lumen selected from the group consisting of an esophagus, uterus, respiratory tract, and bladder.

3. The method of claim 1 wherein occluding the tissue region comprises inflating the occlusion members via a fluid.

4. The method of claim 1 wherein occluding the tissue region comprises expanding the occlusion members via a self-expanding or shape-memory material.

5. The method of claim 1 wherein introducing a hyperthermic or hypothermic fluid and/or gas comprises heating or cooling the fluid and/or gas prior to introduction into the treatment area.

6. The method of claim 1 further comprising visualizing via an endoscope while at least positioning.

7. The method of claim wherein the fluid and/or gas is chilled to less than −5 degrees C.

8. The method of claim 1 further comprising stirring, or circulating the fluid and/or gas within the treatment area such that temperature of the fluid and/or gas is even.

9. The method of claim 1 further comprising introducing, an additional fluid into the treatment area having a temperature which cools or warms the fluid and/or gas.

10. The method of claim 1 wherein the fluid and/or gas comprises water.

11. The method of claim 1, wherein the hyperthermic fluid and/or gas is between 42 degrees Celsius and 100 degrees Celsius.

12. The method of claim 1, wherein the hypothermic fluid and/or gas is between −2 degrees Celsius and −40 degrees Celsius.

13. The method of claim 1, wherein the treatment area is exposed to the hyperthermic fluid and/or gas for a period between 15 seconds and 15 minutes.

14. The method of claim 1, wherein the hypothermic fluid and/or was is between −5 degrees Celsius and −20 degrees Celsius.

15. A method for treating a body cavity or lumen, comprising:
    positioning a tissue region of interest between a distal occlusion member and a proximal occlusion member which are adjustably movable relative to one another via adjustment of a catheter;
    occluding the tissue region to be treated between the occlusion members such that a treatment area is defined therebetween;
    introducing a hyperthermic or hypothermic gel or colloidal suspension into the treatment area such that the tissue region is treated by thermal ablation with the hyperthermic or hypothermic gel or colloidal suspension contacting the tissue region;
    monitoring a first pressure of the hyperthermic or hypothermic gel or colloidal suspension introduced into the treatment area;
    comparing the first pressure against a second pressure within the occlusion members; and
    adjusting the first pressure to be below the second pressure if the first pressure exceeds the second pressure.

16. The method of claim 15 wherein the gel or colloidal suspension comprises a suspension of metal particles, fibers or ions.

17. The method of claim 15 wherein positioning comprises positioning the catheter within a body lumen selected from the group consisting of an esophagus, uterus, respiratory tract, and bladder.

18. The method of claim 15 wherein occluding the tissue region comprises inflating the occlusion members via a fluid.

19. The method of claim 15 wherein introducing a hyperthermic or hypothermic gel or colloidal suspension comprises heating or cooling the gel or colloidal suspension prior to introduction into the treatment area.

20. The method of claim 15 further comprising visualizing via an endoscope while at least positioning.

21. The method of claim 15 wherein the gel or colloidal suspension is chilled to less than −5 degrees C.

22. The method of claim 15 further comprising stirring or circulating the gel or colloidal suspension within the treatment area such that temperature of the gel or colloidal suspension is even.

23. The method of claim 15 further comprising introducing an additional fluid into the treatment area having a temperature which cools or warms the gel or colloidal suspension.

24. The method of claim 15, wherein the hyperthermic gel or colloidal suspension is between 42 degrees Celsius and 100 degrees Celsius.

25. The method of claim 15, wherein the hypothermic gel or colloidal suspension is between −2 degrees Celsius and −40 degrees Celsius.

26. The method of claim 15, wherein the treatment area is exposed to the hyperthermic gel or colloidal suspension for a period between 15 seconds and 15 minutes.

27. The method of claim 15, wherein the hypothermic gel or colloidal suspension is between −5 degrees Celsius and −20 degrees Celsius.

28. A method for treating a body cavity or lumen, comprising:
    positioning a distal end of a treatment catheter within an opening of a body cavity or lumen;
    occluding the opening such that fluid communication is inhibited between an outer surface of the catheter and the opening such that a treatment area is defined within the body cavity or lumen;
    introducing a hyperthermic or hypothermic fluid and/or gas into the treatment area such that a tissue region in the treatment area is treated by thermal ablation with the hyperthermic or hypothermic fluid and/or gas contacting the tissue region;
    monitoring a treatment pressure of the hyperthermic or hypothermic fluid and/or gas introduced into the body cavity or lumen;
    comparing the treatment pressure against an occluding pressure between the catheter and opening; and
    adjusting the treatment pressure to be below the occluding pressure if the treatment pressure exceeds the occluding pressure.

29. The method of claim 28 wherein positioning comprises positioning the catheter distal end within a uterus or bladder.

30. The method of claim 28 wherein occluding comprises inflating an occlusion member via a fluid in proximity to the opening.

31. The method of claim 28 wherein occluding comprises expanding an occlusion members via a self-expanding or shape-memory material.

32. The method of claim 28 wherein introducing a hyperthermic or hypothermic fluid and/or gas comprises heating or cooling the fluid and/or gas prior to introduction into the body cavity or lumen.

33. The method of claim 28 further comprising visualizing via an endoscope while at least positioning.

34. The method of claim 28 wherein the fluid and/or gas is chilled to less than −5 degrees C.

35. The method of claim 28 further comprising stirring or circulating the fluid and/or gas within the body cavity or lumen such that temperature of the fluid and/or gas is even.

36. The method of claim 28 further comprising introducing an additional fluid into the treatment area having a temperature which cools or warms the fluid and/or gas.

37. The method of claim 28 wherein the fluid and/or gas comprises water.

38. The method of claim 28, wherein the hyperthermic fluid and/or gas is between 42 degrees Celsius and 100 degrees Celsius.

39. The method of claim 28, wherein the hypothermic fluid and/or gas is between −2 degrees Celsius and −40 degrees Celsius.

40. The method of claim 28, wherein the treatment area is exposed to the hyperthermic fluid and/or gas for a period between 15 seconds and 15 minutes.

41. The method of claim 28, wherein the hypothermic fluid and/or was is between −5 degrees Celsius and −20 degrees Celsius.

* * * * *